US006432476B1

(12) United States Patent
Corma Canos et al.

(10) Patent No.: US 6,432,476 B1
(45) Date of Patent: Aug. 13, 2002

(54) PRODUCTION OF SEMIOCHEMICAL EMITTERS HAVING A CONTROLLED EMISSION SPEED WHICH ARE BASED ON INORGANIC MOLECULAR SIEVES

(75) Inventors: Avelino Corma Canos; Juan Muñoz Pallares; Eduardo Primo-Yufera, all of Valencia (ES)

(73) Assignees: Consejo Superior de Investigaciones Cientificas, Madrid; Universidad Politecnica de Valencia, Valencia, both of (ES)

( * ) Notice: Subject to any disclaimer, the term of this patent is extended or adjusted under 35 U.S.C. 154(b) by 0 days.

(21) Appl. No.: 09/623,348

(22) PCT Filed: Mar. 3, 1999

(86) PCT No.: PCT/ES99/00054
§ 371 (c)(1),
(2), (4) Date: Oct. 16, 2000

(87) PCT Pub. No.: WO99/44420
PCT Pub. Date: Sep. 10, 1999

(30) Foreign Application Priority Data

Mar. 3, 1998 (ES) .............................................. 9800502

(51) Int. Cl.[7] .................................................. B05D 7/00
(52) U.S. Cl. ........................ 427/215; 427/212; 424/84; 424/417
(58) Field of Search ............................... 427/212, 213.3, 427/215, 421, 424, 427, 430.1, 443.2; 43/107, 108, 114, 115, 121, 122, 123, 132.1, 133, 134, 136; 424/84, 409, 417; 514/964, 965

(56) References Cited

U.S. PATENT DOCUMENTS 4,170,631 A  10/1979 Young et al. ................. 424/19

4,496,585 A * 1/1985 Yoshida et al. ............. 514/514

FOREIGN PATENT DOCUMENTS

WO  WO 96/01052  1/1996
WO  WO 96/39824  12/1996

OTHER PUBLICATIONS

Ginter, D.M. et al, The Chemistry of NaY Crystallization from Sodium Silicate Solutions, 1: 6–30; 1992.
Cremers, A., Ion Exchange in Zeolites, 2:179–193; 1976.
Karge, H.G., Modification of Zeolites and New Routes to Ion Exchange, 273–290; 1992.
McDaniel, C.V. et al, Zeolite Chemistry and Catalysis, 171:285–299; 1976.
Corma, A. et al, Synthesis of MCM–41, 2123–2126; 1997.
Baker, P.S. et al, Field Trials of Synthetic Sex Pheromone Components, 2235–2245; 1990.

* cited by examiner

Primary Examiner—Michael Barr
Assistant Examiner—Rebecca A Blanton
(74) Attorney, Agent, or Firm—Klauber & Jackson

(57) ABSTRACT

This patent presents a method to obtain supports for the controlled and lasting emission of semiochemicals used in the environmental fight against agricultural plagues, due to their noteworthy advantages over other emitters, among which the following stand out:

Adaptation to the emitting needs and to the properties of each semiochemical

The capacity to achieve long useful life times

The non-existent pollution that they produce, due to their chemical nature, they blend in soil Their ease of application since they may be used in the form of pastilles, granulates or powder The possibility of compacting them with different shapes in order adapt them to any support.

13 Claims, 4 Drawing Sheets

PRODUCTION OF SEMIOCHEMICAL EMITTERS HAVING A CONTROLLED EMISSION SPEED WHICH ARE BASED ON INORGANIC MOLECULAR SIEVES

PRIOR ART

Insect plagues cause a drastic reduction of crops and insecticides are the traditional method to combat them. The use of insecticides has problems such as:

- Their toxicity for humans and superior animals, which causes governments to impose more restrictive regulations for the use thereof.
- The lack of selectivity, that converts into the destruction of beneficial insects, or of natural predators of the plague that is to be fought
- The resistance developed by insects which makes it necessary to increase more and more the dosage to maintain the effectiveness thereof.

All of these problems oblige insecticide manufacturers to dedicate more and more resources to R+D in order to obtain better products, but the problem continues to exist.

Society demands respect for the environment but at the same time it requires quality of the agricultural food products, which requires the development of new plague control systems based on environmental methods.

The communication among insects is basically done by means of emitting chemical substances, (semiochemicals); the knowledge of said semiochemical substances and of the information that they transmit, provide an environmental method in order to control the behavior of the insects. By means of the artificial emission of synthetic semiochemicals, a specific message is transmitted to a specific species of insects, inducing a response; if the message is of attraction, the response of the insect will be directed towards the emitter. Taking advantage of this inducing capacity the behavior of insects, techniques that permit the control thereof have been developed. The most important ones are:

- Control, whose purpose is to prevent the occurrence of plagues, to follow their development and to confirm their extinction by means of a count of the captures that are produced in traps provided with an emitter of an attracting semiochemical.
- Sexual confusion, that seeks to prevent the reproduction of insects by means of the emission of amounts of a semiochemical that saturates the receptor organs of the insect preventing it to find members of its same species and of the opposite sex.
- Massive captures, that seek to significantly reduce the insect population, by means of captures, in traps, with an attracting semiochemical. Aside from the attractant, a toxic agent for the insect, a sexual sterilizer, an entomopathogenic microorganism or simply glue where the insect is adhered and dies, may also be placed in the traps.

The low toxicity of semiochemicals, their high specificity (their action is directed towards a single species), the difficult occurrence of resistances and their non-existent polluting impact, represent outstanding advantages in contrast to conventional insecticides.

So that the use of these semiochemical substances is effective it is necessary to have physical supports capable of emitting the semiochemicals in a controlled manner for a sufficient amount of time, in such a way that a concentration in the air capable of causing the desired response in the insect in a continued manner is achieved.

The emitters must comply with a series of requirements so that their use is effective to:

- Provide an adequate emitting speed
- Permit prolonged duration of the emission
- Avoid degradation of the semiochemicals
- Not produce contaminating residues
- Be economical and have easy application Although there is a large variety of emitting supports on the market such as rubber septa (Aldrich Co., UK; The West Co., Pennsylvania; Arthur H. Thomas Co.; Maavit Products, Tel Aviv, Israel), polyethylene pipes (Shin Etsu Chemical Co., Tokyo, Japan), porous plastic laminates (Hercon Lab. Co., New Jersey, USA); capillary fibers (Albany International, Massachusetts, USA), microcapsules (ICI Agrochemicals, Berks, UK), none of these emitting supports comply with all the above mentioned requirements.

Inorganic molecular sieves being used as carriers for semiochemical substances are known from WO-A-9601052, U.S. Pat. No. 4170631 AND WO-A-9639824. Although such carriers are as such inexpensive, the emitters described in these publications are not easily and unexpensively adaptable to different release rates and to the specific needs of different semiochemicals.

The object of this patent is the preparation and use of supports for controlled emission of semiochemicals, based on the modification of the physicochemical properties of zeolites and other inorganic molecular sieves, in such a way that they provide an emission kinetics adapted to the specific properties of each pheromone.

DESCRIPTION OF THE INVENTION

Inorganic molecular sieves (IMS) have a complex network formed by an assembly of micro or meso pores (Ø>14 Å) and cavities, providing the assembly with a high specific surface and a high adsorption capacity. The most important IMS are zeolites, chemically they are aluminosilicates with the Al in tetrahedral coordination, giving rise to a negative charge that must be compensated for by intracrystalline cations. Another group of IMS are aluminophosphates (AlPOs) with Al and P in tetrahedral coordination forming an electrically neutral network and therefore, without compensation cations and the SAPOs and MAPOs, in which aside from aluminum and phosphorus, there are other elements such as Si and transition metals respectively.

In zeolites, we can adjust the adsorption force by modifying the chemical composition of the network, keeping the structure constant, as it happens when several faujasites with different Si/Al ratios are used; upon modifying this ratio the number of adsorption centers and the force thereof vary. The variation of the Si/Al ratio can be varied by means of synthesis of the zeolite (D. M. Ginger (1992). "The chemistry of NaY crystallization from sodium silicate solutions". Molecular Sieves. 1:6–30) or post synthesis, mainly by means of treatment with steam.

Another variable that allows us to adjust the adsorption force, in the case of zeolites, is the modification of the cation charge/radius ratio: Upon exchanging a cation for another one with a smaller charge/radius ratio increases the charge fraction on the oxygen bridge, therefore increasing the interaction of a polar organic semiochemical adsorbed on the zeolite. Cation exchanges tend to be carried out by means of treatment in liquid phase (A. Cremers (1976). "Ion exchange in zeolites". Molecular Sieves. 2:179–193) or in solid phase (H. G. Karge, (1992). "Modification of zeolites and new routes to ion exchange". Zeolites Microporous Solids: Synthesis, structure and reactivity. 273–290). In this way, fixation by lipophile for low polarity pheromones can also be varied.

If it is a matter of zeolites, in many cases, we can give them Bronsted acidity in order to cause the formation of hydrogen bonds with the adsorbed semiochemical, when this has functional groups capable of forming said bonds, which causes an increase of retention. The introduction of protons can be done by acid treatment (C. V. McDaniel, P. K. Maher (1976). "Zeolite chemistry and catalysis". ACS Monograph. 171:285–299) or exchange with $NH_4^+$ and calcination (A. P. Bolton (1976). "Experimental methods in catalytic research". Academic Press. 2: 1–23) or by direct calcination on samples that do not contain alkaline compensation cations, but rather amines or quaternary ammonium cations.

In IMS we can control the diffusion of molecules through the network by modifying the dimensions of pores and cavities and the size of the compensation cations if there are any. A small pore, but sufficiently large so as to permit the entry of the semiochemical, makes the diffusion thereof difficult and therefore, the semiochemical will have a lower emitting speed. Diffusion can also be controlled by varying the size of the cations: the larger the size the less diffusion and slower emitting speed. The modification of the pore size can be done by modifying the conditions of synthesis of the IMS (A. Corma, Q. Kan, M. T. Navarro, J. Perez-Pariente and F. Rey (1997) "Synthesis of MCM-41 with different pore diameters without addition of auxiliary organics" Chemical Materials. In press).

On the other hand, the fact of compacting the IMS with the adsorbed semiochemical provides us with two more variables, not dependent on the nature of the IMS, in order to control the kinetics:

The compacting pressure: When compacting is done at a higher pressure the amount of semiochemical adsorbed in macropore is reduced and it is forced to diffuse through the network in order to go outside, therefore reducing, the emitting speed.

The surface/weight ratio of the finally obtained form. If the surface/weight ratio is high the semiochemical reaches the surface before, increasing the emitting speed.

Figure 1:
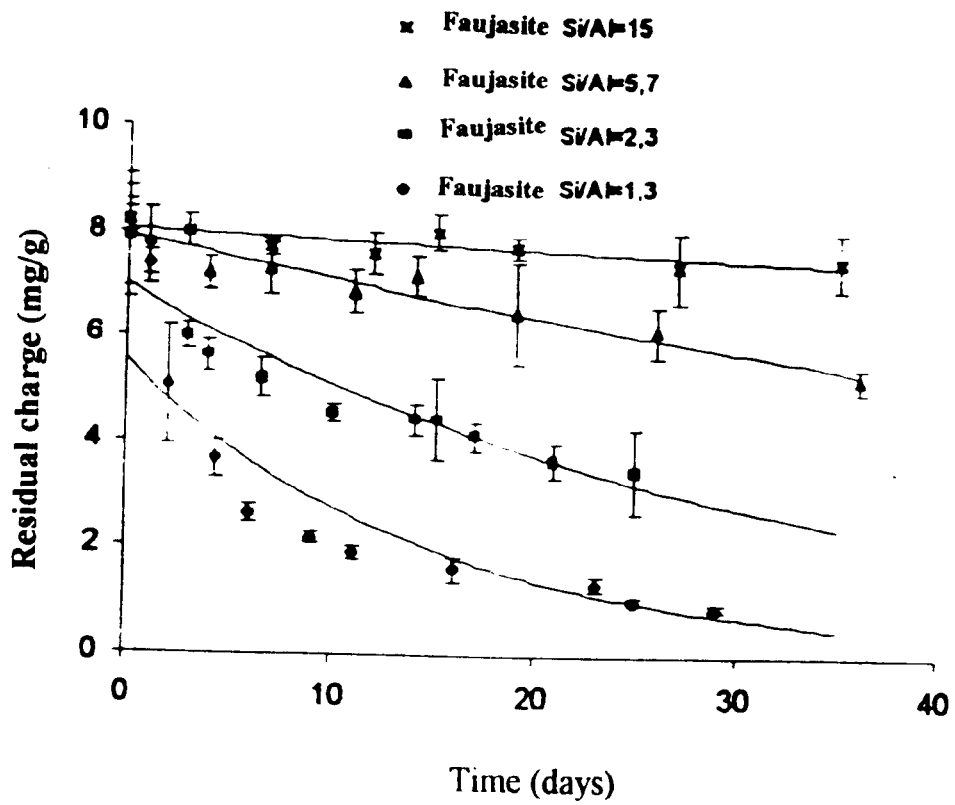
FIG. 1 is a graph of the emission kinetics of a zeolite catalyst prepared in accordance with the invention.

The present invention as claimed, presents a method for preparing supports for controlled and lasting emission of semiochemicals used in the environmental fight against agricultural plagues, due to their outstanding advantages over other emitters, among which the following can be emphasized:

Adaptation to the emitting needs and to the properties of each semiochemical.

The capacity to achieve longer useful life times

The non-existent pollution that they produce, since due to their chemical nature, they blend in the agricultural soil Their ease of application since they can be used in the form of tablets, granulates, conglomerates or powder.

The possibility of compacting them with different shapes in order to adapt them to any support.

EXAMPLES

Several examples are given hereinafter of several examples of modification of the physicochemical properties of zeolites in order to adapt them to predetermined emission kinetics, taking N-decyl alcohol, sexual pheromone of the *Agrotis segeton* and of the *Cydia pomonella* as the standard.

The emission kinetics of the semiochemicals adsorbed in zeolite is determined by the following method:

1. Impregnation of the zeolite: This is done by adding to the powdered zeolite, a solution of the semiochemical in dichloromethane and intense stirring for 1 hour, subsequently eliminating the dichloromethane. The impregnated zeolite is homogenized by stirring for half an hour and then it is compacted in a press, to form tablets.

2. Aeration and aging: The tablets are kept at 25° C. and with controlled aeration for 45 days. Periodically the amount of semiochemical that remains in the pastilles is determined, by means of extraction with soxhlet with the suitable solvent and gas chromatography. The kinetics obtained are first-rate.

The determination of the punctual emitting speed is done by using a thermostated aerator, inside of which the pastille of IMS impregnated with pheromone is placed. A controlled air flow is circulated, with a constant temperature for a specific amount of time. When it comes out, the air passes through a cartridge of adsorbent, generally, a Sep-pak $C^{18}$, where the pheromone is retained. Subsequently the cartridge is removed and the amount of pheromone emitted is determined by quantitative gas-liquid chromatography.

Example 1

Modification of the Si/Al ratio of isostructural zeolites for controlled emission of the pheromone: n-decyl alcohol.

Compared Emitting Supports:

Zeolite XNa, Commercial ($[Al_{83}Si_{109}O_{384}]$ $Na_{83}$*240240$H_2O$ with Si/Al ratio=1.3)

Zeolite YNa, Commercial ($[Al_{53}Si_{139}O_{384}]$ $Na_{53}$*240240$H_2O$ with Si/Al ratio=2.6)

Zeolite USYNa, Modified ($[Al_{28}Si_{164}O_{384}]$ $Na_{28}$*240240$H_2O$ with Si/Al ratio=5.7)

Zeolite USYNa, Modified ($[Al^{12}Si_{180}O_{384}]$ $Na_{12}$*240240$H_2O$ with Si/Al ratio=15)

Prior Treatments:

Commercial zeolite XNa and YNa zeolite (CBV-100) were used that were treated, in order to eliminate acidity residue, with 0.5M NaCl solution with a liquid/solid ratio: 6/1, stirring at 80° C. for 6 hours; then it was vacuum filtered and kept 12 hours in an oven at 100° C.

Preparation of Zeolites with the Suitable Si/Al Ratio:

USY 5.7 is obtained starting with YNa, following the following method:

1. Exchange of $Na^+$ by $NH_4^+$, by means of treatment with 2.5M $NH_4Cl$ with a liquid/solid ratio: 10/1, at 80° C. for 1 h with stirring. The sample is filtered and washed with water at 50° C. until there is an absence of chlorides. Then it is dried in an oven at 100° C. for 12 h. This treatment is done twice.

2. Hydrothermal treatment with an atmosphere 100% steam according to the following program:

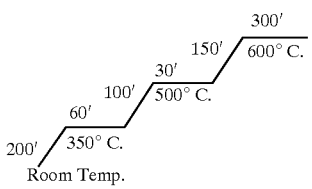

Room Temp.

3. Another exchange is carried out like the one in step 1 and it is calcined according to the following program:

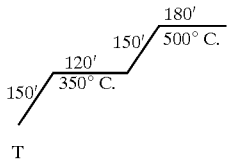

T step 3 is repeated twice.

4. Elimination of Al outside the network. It is treated with 0.4M ammonium hexafluorosilicate by means of perfusion at 80° C., in the presence of $ACNH_4$, for 4 h and it is washed carrying the Al outside of the network. The solid is dried in an oven at 80° C. for 2 h. The chemical analysis gives a Si/Al ratio of 5.7 with an elimination of 88% of the Al outside the network and the X-ray diffraction, show the conservation of the crystallinity with regard to the YNa (CBV-100).

5. Finally, ammonium USY is exchanged with $Na^+$ by means of treatment with 0.5M NaCl with liquid/solid ratio: 6/1, at 80° C. for 6 h. It is filtered and washed until there is an absence of chlorides. The chemical analysis shows an exchange of 85%.

USY 15 is obtained like the 5.7, but repeating the calcination described in step 2, with a final temperature of 750° C.

The kinetics obtained are shown in FIG. 1: Influence of the Si/Al ratio on emission kinetics. The increase of retention is observed when the Si/Al ratio increases. The increase of the Si/Al ratio means a reduction of polarity. The test is carried out with an initial charge of 8 mg of pheromone/g of zeolite and tablets with a 13 mm ∅, with a compacted weight of 0.55 g and a pressure of $3T/cm^2$.

Example 2

Modification of the Bronsted acidity of isostructural zeolites and with the same Si/Al ratio, for controlled emission of pheromone: n-decyl alcohol.

Compared Emitting Supports:

Zeolite YNa, Commercial ($[Al_{53}Si_{139}O_{384}]$ $Na_{53}*240240H_2O$)

Zeolite YHNa 10%, Modified ($[Al_{53}Si_{139}O_{384}]$ $Na_{47.7}H_{5.3}*240240H_2O$)

Zeolite YHNa 50%, Modified ($[Al_{53}Si_{139}O_{384}]$ $Na_{26.5}H_{26.5}*240240H_2O$)

Zeolite YHNa 80%, Modified ($[Al_{53}Si_{139}O_{384}]$ $Na_{10.6}H_{42.4}*240240H_2O$)

Preparation of Zeolites with the Suitable Acidity:

Zeolite YNa is subjected to exchange of Na by H, by means of treatment with 0.5M $NO_3NH_4$ with liquid/solid ratio: 6/1, for 6 hours at 80° C. and stirring. The sample is washed, dried for 12 hours at 100° C. The sample is calcined in a muffle following the following heating program:

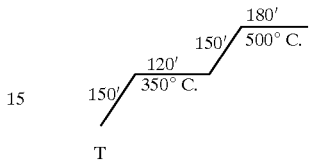

T

With this first treatment (exchange+calcination), an exchange of 50% is obtained, two repetitions of this treatment on YHNa 50% lead to an exchange of 80%. In order to obtain the YHNa 10% the described treatment is carried out but using 0.2M $NO_3NH_4$ instead of 0.5M. The % of exchange are determined by chemical analysis by means of atomic absorption. X-ray diffraction spectrum are made on the sample that indicate the crystallinity conservation.

Figure 2:
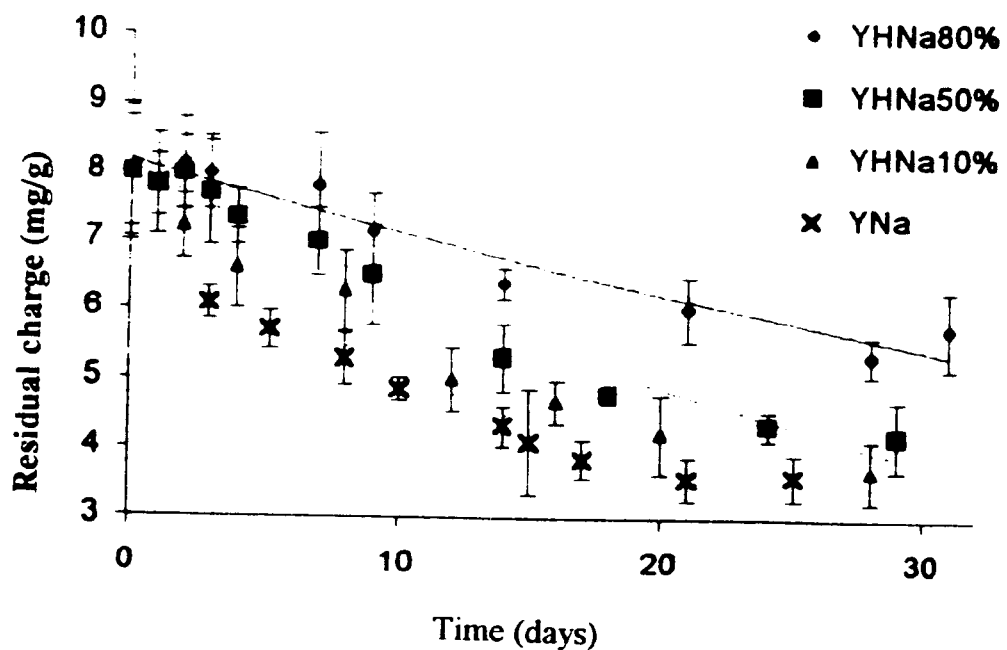
FIG. 2 is a graph of the emission kinetics of a zeolite catalyst prepared in accordance with the invention that particularly demonstrates the influence of acidity an such emission kinetics.

The kinetics obtained are shown in FIG. 2: Influence of acidity on emission kinetics. A clear correlation between the acidity of the zeolite and the kinetics is produced: the higher the acidity the slower the kinetics. The test is carried out with an initial charge of 8 mg of pheromone/g of zeolite. Tablets with a 13 mm ∅, a weight of 0.6 g and a surface/weight ratio: 6.7 $cm^2/g$. are used. The compacting pressure is $3T/cm^2$.

Example 3

Modification of the compensation cation of isostructural zeolites and with the same Si/Al ratio, for controlled emission of pheromone: n-decyl alcohol.

Compared Emitting Supports:

Zeolite XNa, ($[Al_{83}Si_{109}O_{384}]$ $Na_{83}*240240H_2O$)

Zeolite XNaCs with 40% Cs,($[Al_{83}Si_{109}O_{384}]$ $Na_{43.2}Cs_{39.8}*240240H_2O$)

Previous Treatments

Commercial zeolite XNa is used, which is treated to remove the acidity residues with the same method as described in example 1.

Preparation of Zeolites with the Suitable Cation:

Zeolite XNa, free of acidity, is subject to a process of exchange of the Na by Cs. It is treated with a 1M ClCs solution with liquid/solid ratio: 10/1 at 80° C. for 1 h, with stirring. It is washed until there is an absence of chlorides. It is dried in an oven at 100° C. for 12 hours. The exchange is repeated for a second time. The chemical analysis indicates an exchange of 40%.

Figure 3:
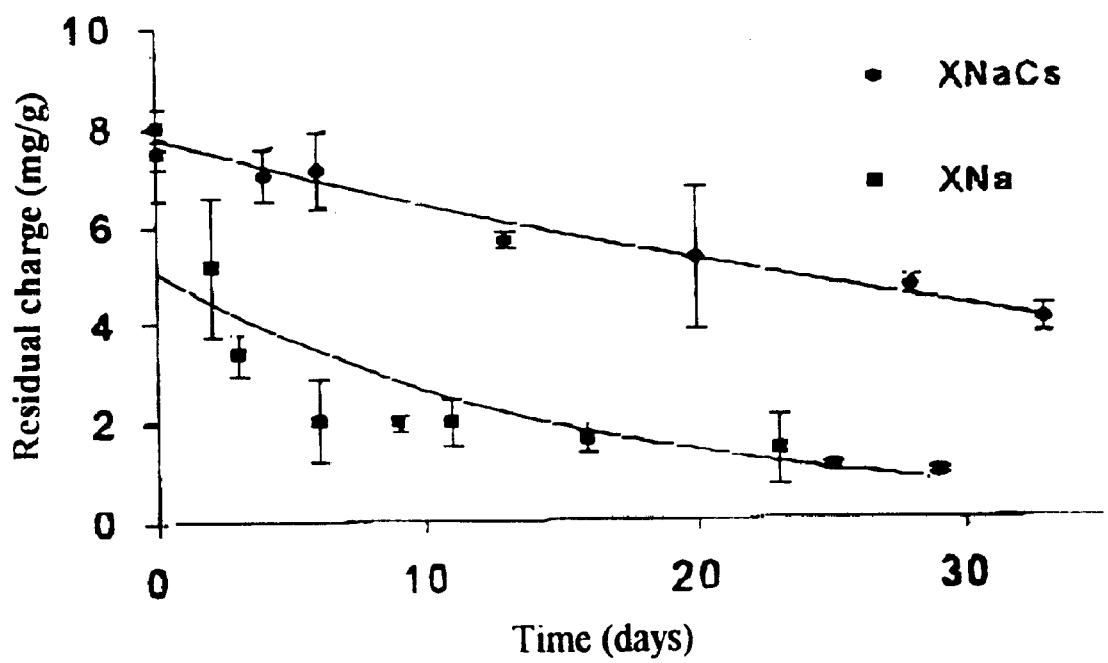
FIG. 3 is a graph demostrating the emission kinetics of a zeolite catalyst prepared in accordance with Example 3, particularly illustrating the effect of the compensation cation on such emission kinetics.

The kinetics obtained are shown in FIG. 3: Influence of the compensation cation on emission kinetics. Upon reducing the charge/radius ratio of the compensation cation the retention increases. The test is carried out with an initial charge of 8 mg of pheromone/g of zeolite. Tablets with a 13 mm ∅, a weight of 0.5 g, compacted with a pressure of $3T/cm^2$ are used.

Example 4

Modification of the pore size in AlPOs, for controlled emission of semiochemical trimedlure Compared Emitting Supports:

AlPO$_4$11 ([Al$_{20}$P$_{20}$O$_{80}$]); pore 6.3×3.9 Å

AlPO$_4$5 ([Al$_{12}$P$_{12}$O$_{48}$]); pore 7.3 Å

VP15 ([Al$_{18}$P$_{18}$O$_{72}$]); pore 12.1 Å

Preparation of AlPOs with the Suitable Pore Size:

AlPO$_4$11: The synthesis gel is formed with hydrated alumina (73.7% Catapal B in Al$_2$O$_3$), 85% H$_3$PO$_4$ and dipropylamine. After stirring, it is subjected to treatment in an autoclave, for 16 hours at 195° C. Finally, the sample is calcined for 1 h at 540° C., in a N$_2$ flow and for 3 h, at the same temperature, in a dry air flow.

AlPO$_4$5: The synthesis gel is formed with hydrated alumina (73.7% Catapal B in Al$_2$O$_3$), 85% H$_3$PO$_4$ and trimethylamine. After aging and stirring it is subjected to treatment in an autoclave, for 25 h at 190° C. and 23 h at 170° C. After washing the sample, it is subjected to the following calcination program:

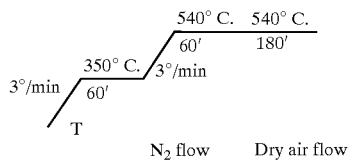

VP15: The synthesis gel is formed with hydrated alumina (70% Catapal in Al$_2$O$_3$), 85% H$_3$PO$_4$ and dipropylamine. After stirring it is subjected to the following treatment in an autoclave: starting from room temperature and by means of a ramp of 2° C./min., 140° C. is reached, where the sample remains for 3 h. After several decantations the product is separated and subjected to the following calcination program:

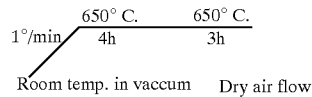

Figure 4:
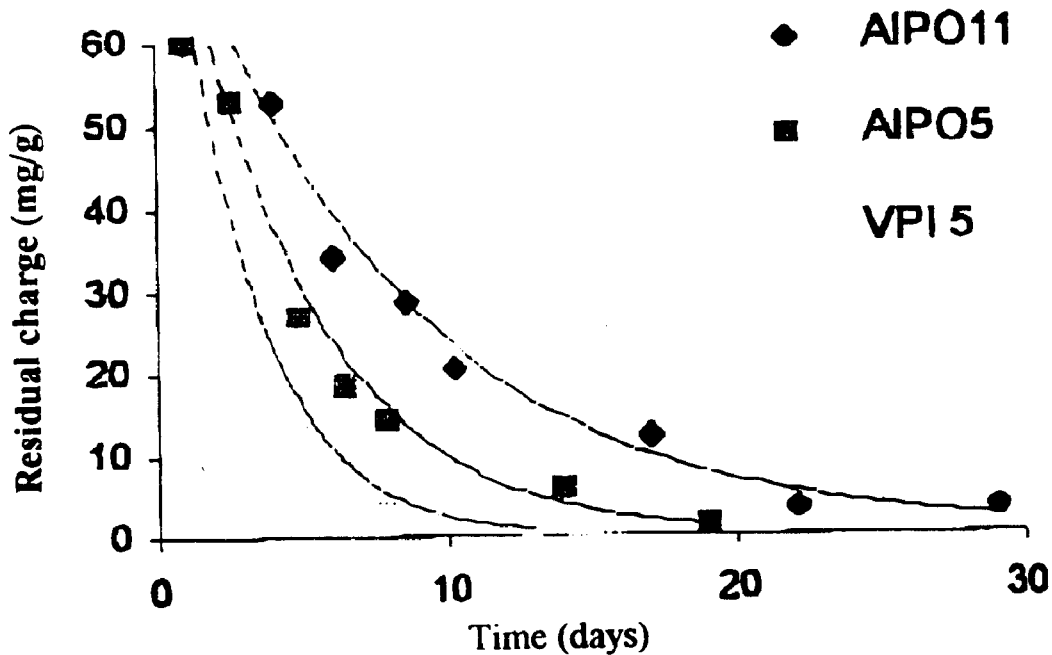
FIG. 4 is a graph demonstrating the influence of pore size on the emission kinetics of catalyst supports prepared in accordance with the present invention.

The kinetics obtained are shown in FIG. 4: Influence of the pore size on emission kinetics. Upon reducing the pore size the kinetics is slower. The test is carried out with an initial charge of 140 mg of semiochemical/g of AlPO. Tablets with a 5 mm ⌀, a weight of 0.1 g, compacted with a pressure of 3T/cm$^2$ are used.

Example 5

Modification of the compression pressure on zeolites for the controlled emission of pheromone: n-decyl alcohol.

Emitting Support

Zeolite YHNa 80%, Modified, ([Al$_{53}$Si$_{164}$O$_{384}$] Na$_{10.6}$H$_{42.4}$*240H$_2$O)

Previous Treatments:

Zeolite YHNa 80% is obtained from zeolite YNa (CBV-100), by means of the method described in example 2.

Preparation of Zeolites with the Suitable Compression Pressure:

Two zeolite YHNa 80%-pheromone systems are prepared and compressed forming pastilles, at two different pressures (3 and 10 T/cm$^2$).

Figure 5:
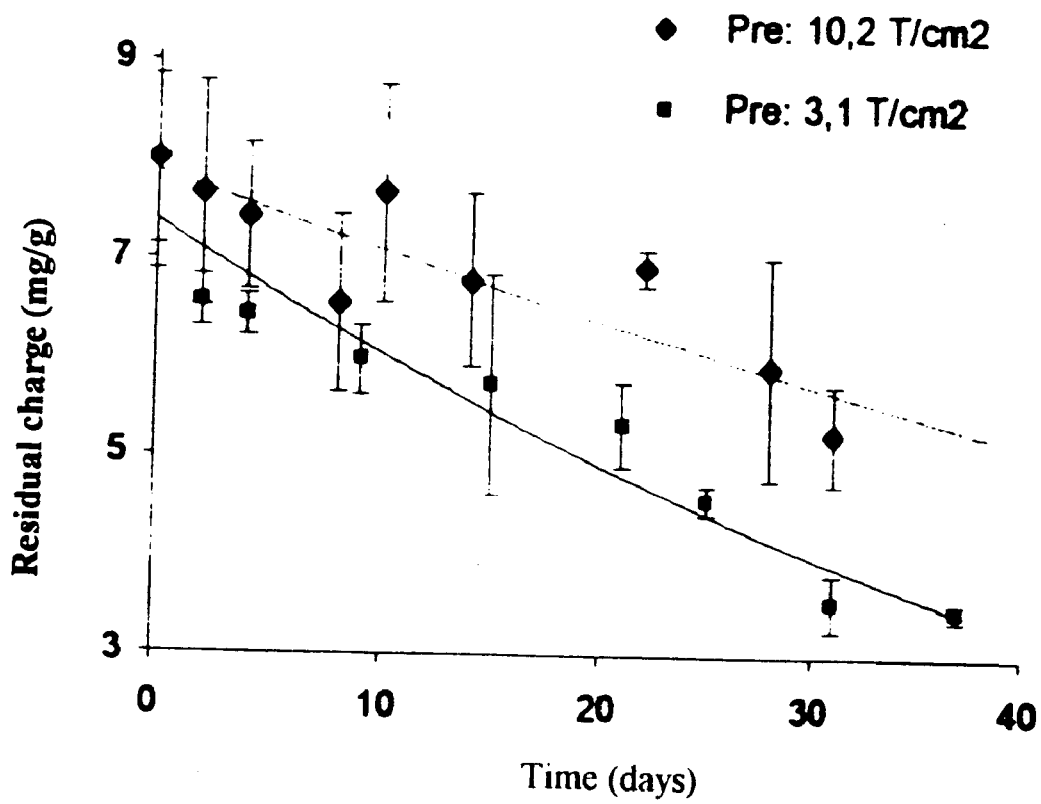
FIG. 5 is a graph demonstrating the effect of compression pressure on emission kinetics of catalyst supports in accordance with the present invention.

The kinetics obtained are shown in FIG. 5: Influence of the compression pressure on emission kinetics: An increase of retention is obtained with the increase of compression pressure. The test is carried out with an initial charge of 8 mg of pheromone/g of zeolite. Tablets with a 5 mm ⌀, a weight of 0.07 g with a surface weight ratio: 10.9 cm$^2$/g are used.

Example 6

Modification of the surface/weight ratio of the zeolite pastilles, for the controlled emission of pheromone: n-decyl alcohol.

Emitting Support:

Zeolite YHNa 80%, Modified, ([Al$_{53}$Si$_{164}$O$_{384}$] Na$_{10.6}$H$_{42.4}$*240H$_2$O)

Previous Treatments:

Zeolite YHNa 80% is obtained from zeolite YNa (CBV-100), by means of the method described in example 2.

Preparation of Zeolite Tablets with the Suitable Surface/weight Ratio:

Two zeolite YHNa 80%-pheromone systems are prepared, one is pressed forming pastilles with a 13 mm ⌀, with a surface/weight ratio: 6.7 cm$^2$/g, the other one is compressed forming tablets with a 5 mm ⌀ with a surface/weight ratio: 10.9 cm$^2$/g. The two systems are compressed at the same pressure.

Figure 6:
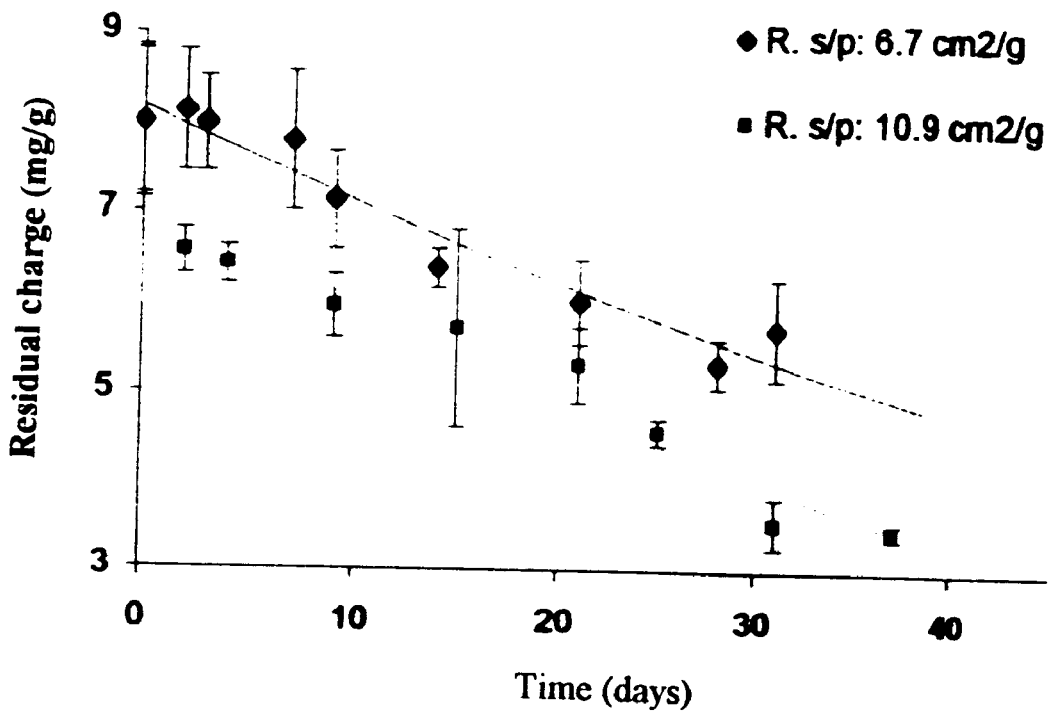
FIG. 6 is a graph demonstrating the effect on emission kinetics of catalyst supports having variations in the weight/surface ratio.

The kinetics obtained are shown in FIG. 6. Influence of the weight/surface ratio on emission kinetics. An increase of emitting speed is obtained when the surface/weight ratio is large. The test is carried out with an initial charge of 8 mg of pheromone/g of zeolite, compacted with a pressure of 3T/cm$^2$.

Example 7

Modification of a commercial zeolite for the application of the semiochemicals 2,3- and 2,5-dimethylpyracine (DMPs), attractants of Cereatitis capitata (P. S. Baker, P. E. Howse, R. N. Ondarza and J. Reyes (1990). "Field trials of synthetic sex pheromone components of the male Mediterranean fruit fly (Diptera:tephritidae) in southern Mexico". Journal of Economic Entomology. 86,6:2235–2245), in such a way that the emission kinetics of DMPs is adequate so that the application is effective in a grapefruit field.

Compared Emitting Supports:

Zeolite YHNa 50%, Modified, ([Al$_{53}$Si$_{139}$O$_{384}$] Na$_{26.5}$H$_{26.5}$*240H$_2$O)

8 mm rubber septa

Previous Treatments:

Zeolite YHNa 50% is obtained from zeolite YNa (CBV-100), by means of the method described in example 2.

Method of Application:

The initial charge of the emitters is of 10 mg of a 50% mixture of 2,3- and 2,5-dimethylpyracine.

Yellow delta traps with an exchangeable floor impregnated with glue are used. The traps are placed on alternate trees (10 m. between traps). Periodically the captures are counted and the emitters are collected in order to analyze them in the laboratory by means of extraction and quantitative gas-liquid chromatography.

Results

Figure 7:
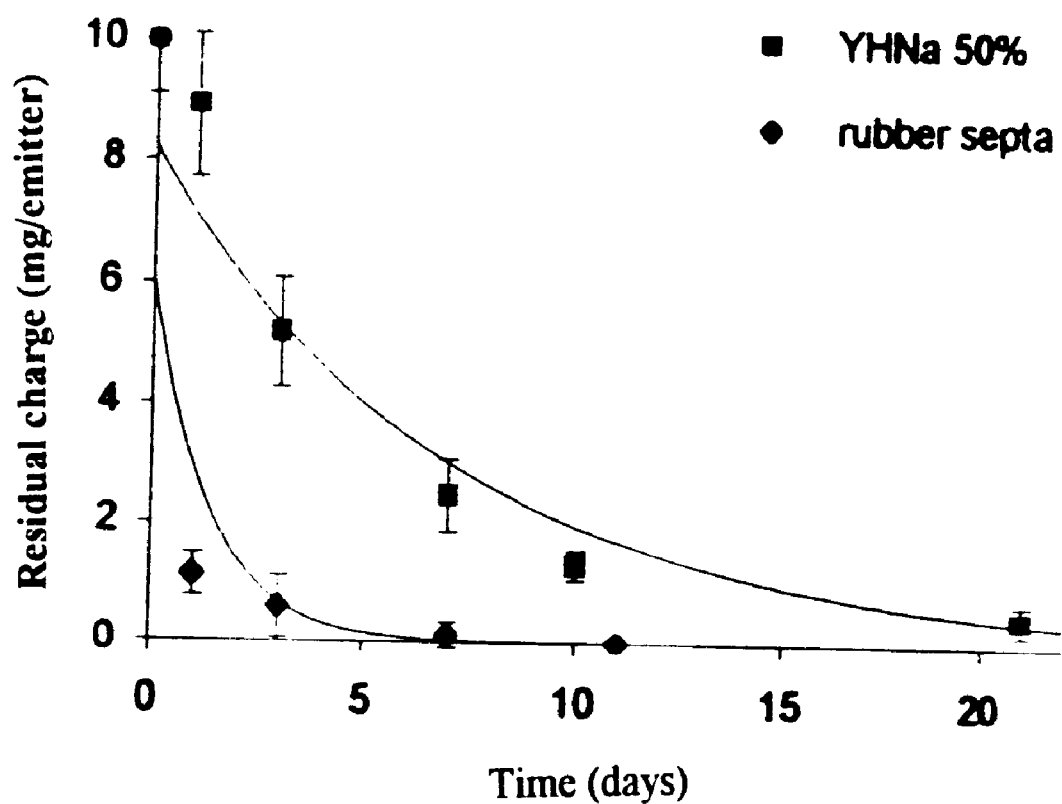
FIG. 7 is a graph presenting the comparison of the field kinetics of zeolite YHlNa 50% with reference to rubber septa as to emissions of dimethylpyracines.

The emission kinetics of the compared systems are shown in FIG. 7: Comparison of the field kinetics of zeolite YHNa 50% with regard to rubber septa in the emission of dimethylpyracines. A gentler kinetics of the zeolite that keeps the activity for more time is observed. The useful life time of zeolite is 45 days with regard to 8 days of rubber septa. Zeolite captures 3 times more flies than rubber septa.

What is claimed is:

1. A process for preparing an emitter for controlled and durable release of a semiochemical substance from a support having a network of micropores, mesopores and macropores, the support being selected from the group consisting of zeolites and of inorganic molecular sieves selected from aluminosilicates and aluminophosphates, wherein the process comprises adapting physiochemical properties of the support to characteristics of the semiochemical substance and to specific needs of release kinetics, whereby said properties are adapted to said semiochemical substance and to said specific needs of release kinetics by modifying at least one property selected from the group consisting of Si/Al ratio, acidity, compensation cations, pore size, compression degree and surface/weight ratio of the support, whereby, for reducing the release rate, the support is subjected to at least one treatment selected from the group consisting of increasing the number and strength of the adsorption centers of the support by increasing the Si/Al ratio of the support, and impregnating the support with the semiochemical substance;

providing Bronsted acidity to the support by introducing protons into the support and impregnating the support with a semiochemical substance having functional groups being capable of forming hydrogen bonds with the support;

reducing cation charge/radius ratio of a support having compensation cations and impregnating the support with polar semiochemical substance;

reducing pore sizes of the support, and impregnating the support with a semiochemical substance having a size being smaller than at least a portion of the sizes of the pores of the support;

impregnating the support with the semiochemical substance and subjecting the impregnated support to compactation by applying pressure; and impregnating the support with the semiochemical substance and reducing the surface/weight ratio of the substance support by compactation.

2. A process according to claim 1, wherein the zeolite is selected from the group consisting of Zeolite XNa, zeolite YNa, zeolite USYNa, zeolite YHNa and zeolite XNaCs.

3. A process according to claim 1, wherein the inorganic molecular sieve is selected from the group consisting of aluminophosphates, silicon aluminophosphates and aluminophosphates comprising transition metals.

4. A process according to claim 1, wherein the support is in the form of a powder, and wherein the support is impregnated with a solution comprising the a semiochemical substance and a solvent, forming a dispersion by adding the solution to the powder, stirring the dispersion, eliminating the solvent, and homogenizing the impregnated support.

5. A process according to claim 1, wherein the semiochemical substance is a sexual pheromone.

6. A process according to claim 1, wherein the semiochemical substance is n-decyl alcohol.

7. A process according to claim 1, wherein the semiochemical substance is dissolved in dichloromethane.

8. A process according to claim 1, wherein the semiochemical substance is selected from 2,3-dimethylpyracine, 2,5-dimethylpyracine and mixtures thereof.

9. A process according to claim 1, wherein the impregnated support is formed into a powder.

10. A process according to claim 1, wherein the impregnated support is formed into a granulate.

11. A process according to claim 1, wherein the impregnated support is formed into a conglomerate.

12. A process according to claim 1, wherein the impregnated support is formed into tablets.

13. An emitter for controlled and durable release of a semiochemical substance which has been prepared in accordance with the process of claim 1.

* * * * *